United States Patent [19]

Debay

[11] Patent Number: 4,607,047

[45] Date of Patent: Aug. 19, 1986

[54] N-(ALLYL-2-PYRROLIDINYLMETHYL)-2-METHOXY-4-AMINO-5-METHYLSULFAMOYL BENZAMIDE ANTI PLATELETS AGGREGATION AGENT

[75] Inventor: André Debay, Paris, France

[73] Assignee: Societe d'Etudes Scientifiques et Industrielles de l'Ile-De-France, Paris, France

[21] Appl. No.: 638,403

[22] Filed: Aug. 7, 1984

[30] Foreign Application Priority Data

Aug. 10, 1983 [FR] France ................................ 83 13141

[51] Int. Cl.4 ..................... A61K 31/40; C07D 207/09
[52] U.S. Cl. .................................... 514/428; 548/567
[58] Field of Search .......................... 548/567; 514/428

[56] References Cited

U.S. PATENT DOCUMENTS

| | | | |
|---|---|---|---|
| 4,263,316 | 4/1981 | Thominet et al. | 548/567 X |
| 4,294,828 | 10/1981 | Thominet et al. | 548/567 X |
| 4,351,770 | 9/1982 | Ogata et al. | 548/567 |
| 4,405,636 | 9/1983 | Perrot et al. | 548/571 X |
| 4,499,019 | 2/1985 | Thominet et al. | 548/567 X |

FOREIGN PATENT DOCUMENTS 2083033A  3/1982  United Kingdom ................ 548/567

OTHER PUBLICATIONS

Evans, et al.; J. Exp. Med.; 128: 877–894 (1968).
Mustard, et al.; J. Lab. Clin. Med.; 64: pp. 548–558 (1964).

*Primary Examiner*—Joseph Paul Brust
*Attorney, Agent, or Firm*—Fitzpatrick, Cella, Harper & Scinto

[57] ABSTRACT

N-(1-allyl-2-pyrrolidinylmethyl) 2-methoxy-4-amino-5-methylsulphamoyl benzamide and its pharmacologically acceptable salts thereof are taught to be useful in treating a subject suffering from platelet dysfunction in thrombo-embolic disorders.

2 Claims, No Drawings

N-(ALLYL-2-PYRROLIDINYLMETHYL)-2-METHOXY-4-AMINO-5-METHYLSULFAMOYL BENZAMIDE ANTI PLATELETS AGGREGATION AGENT

The present invention concerns a novel application of N-(1-allyl-2-pyrrolidinylmethyl) 2-methoxy 4-amino 5-methylsulphamoyl benzamide, hereinafter referred to as 'the compound'.

The results of biochemical studies in vitro have shown that the compound inhibits platelet aggregation which is caused by adenosine phosphate, and that it also inhibits potentiation by CLONIDINE of the aggregation due to adenosine phosphate.

Careful observations in respect of that mechanism in rabbits have shown that the compound does not modify the uptake of serotonin by the platelets, but inhibits the release thereof, which is induced by adrenaline, from the same platelets.

Finally, the compound opposes the platelet aggregating action of collagen, prolonging the latency phase. It inhibits the release of serotonin by the platelets under the effect of collagen, being shown in that effect to be thirteen times more active than aspirin.

Tests have also been made in vitro on human platelets; under those conditions, it was found that the compound inhibits the second phase of aggregation induced by thrombin and the aggregation caused by collagen, adrenaline and serotonin.

In addition, it inhibits the release of serotonin, induced by thrombin or collagen. It also inhibits the release reaction of intra-platelet material which is caused by adrenaline, as is proven by inhibition of the second phase of aggregation which is usually associated with that release.

In vivo tests in animals have confirmed the anti-aggregating effect of the compound, which modifies the conditions of formation of a caused vascular thrombus.

Anomalies in the platelet function have been reported in the course of various thrombo-embolic disorders such as cardiac ischaemia, cerebro-vascular attack, idiopathic veinous thrombosis, and likewise in the case of hyperlipoproteinaemia, hypertension, and diabetes, or in heavy smokers, all being well-known symptoms in respect of aggravation of cardiovascular risk.

Although under those conditions the pathogenetic role of platelet dysfunction has not been definitively established, various medicaments which are assumed to act by interfering with the platelet function have been widely used. Reference may be made for example to aspirin, dipyridamole and sulphinpyrazone. Pharmacological studies among animals have shown that the compound had only a very weak action on the central dopaminergic receptors; in particular, high doses are required to counteract the conventional effects with apomorphine, comprising climbing and stereotypies in rodents. It can be said therefore that the undesirable neurological effects are very limited with that medicament.

The following pharmacological results illustrate the activity of the compound on platelet aggregation, the potentiation of such aggregation, the uptake of serotonin (the chemical name for which is 5-hydroxytryptamine) by the platelets and the release reaction of such platelets. This study was carried out on rabbits:

An inhibiting effect on the aggregation of platelets, caused by adenosine phosphate is observed.

The compound inhibits potentiation (induced by 5-hydroxytryptamine) of aggregation of the platelets, caused by adenosinephosphate, at a level of $IC_{50}$ (inhibiting concentration 50) of 19 $\mu M$. It is 63 times less powerful than METHYSERGIDE as a 5-hydroxytryptamine antagonist.

The compound inhibits potentiation (induced by adrenaline) of platelet aggregation caused by adenosinephosphate, at a level of $IC_{50}$ of 10 $\mu M$. It is 20 times less powerful than PHENTOLAMINE as an adrenaline antagonist.

The anti-adrenergic effect of the compound ($IC_{50}=29.5$ $\mu M$) occurs, at least in part, by means of blocking of the alpha-2 receptors. That is demonstrated by the inhibition effect which is obtained by the compound of the invention in respect of potentiation (induced by CLONIDINE) of platelet aggregation caused by adenosinephosphate, which is an effect that involves the alpha-2 receptors. The compound is twice as active as MIANSERINE as an alpha-2 antagonist.

The compound does not significantly affect uptake of 5-hydroxytryptamine which is marked with carbon 14, by the platelets in a rabbit ($IC_{50}>100$ $\mu M$).

The compound counteracts the action of collagen on the platelets. That is demonstrated by:

a. prolongation of the typical latency phase which precedes aggregation of the platelets induced by collagen, b. inhibition of the aggregation effect induced by collagen, and c. inhibition of the release reaction by the platelets (release of the carbon 14-marked 5-hydroxytryptamine, which is induced by collagen), with an $IC_{50}$ of 1.8 $\mu M$. The compound of the invention is 13 times more powerful than aspirin, which is well known for inhibiting the platelet release reaction.

The compound inhibits the release of carbon 14-marked 5-hydroxytryptamine (induced by adrenaline) from rabbit platelets, at an $IC_{50}$ of 100 $\mu M$.

All those results agreeing, the following study was carried on on human platelets in vitro, before proceeding to therapeutic applications. It relates to the effects of the compound according to the invention, in regard to aggregation induced by thrombin, collagen, adrenaline, and 5-hydroxytryptamine, and with regard to the release of carbon 14-marked 5-hydroxytryptamine, by thrombin, adrenaline and collagen. The series of tests led to the following results:

The compound does not influence the primary aggregation of platelets, but inhibits the second phase of aggregation, induced by thrombin (3.3 units/ml PRP).

The compound inhibits the aggregation of platelets, which is induced by collagen.

The compound inhibits both the first and the second phases of aggregation of the platelets, which is induced by adrenaline.

The compound inhibits aggregation of platelets, which is induced by 5-hydroxytryptamine.

The compound does not influence the uptake of carbon 14-marked 5-hydroxytryptamine, by platelets.

The compound inhibits the release of carbon 14-marked 5-hydroxytryptamine, which is induced by thrombin, from platelets.

The compound inhibits the release of marked 5-hydroxytryptamine, which is induced by collagen, from platelets.

The compound inhibits the release reaction of the platelets, which is induced by adrenaline, as witnesses inhibition of the second phase of aggregation which is usually associated with release of the intra-platelet material.

The compound according to the invention, with the data obtained in the course of studies on animals having been confirmed on human platelets, can be proposed for therapeutic uses, as an anti-aggregating medicament, and in accordance with the aim sought to be achieved, at dosages varying from 15 mg to 150 mg per day and orally. The compound is generally used associated with an excipient which is inert with respect to the active ingredient, in different conventional galenical forms. Although the injectableor rectal form is possible, the oral form is preferred: use will therefore be made rather of compressed tablets, capsules, syrups or drinkable solution, facilitating spreading out the treatment over the course of a day.

In conclusion, there is proposed N-(1-allyl-2-pyrrolidinylmethyl)2-methoxy 4-amino 5-methylsulphamoyl benzamide as a novel medicament having a platelet anti-aggregating effect.

I claim:

1. A method of treating a subject suffering from platelet dysfunction in thrombo-embolic disorders which comprises administering to said subject in need thereof an amount sufficient to inhibit platelet aggregation of N-(1-allyl-2-pyrrolidinylmethyl)2-methoxy-4-amino-5-methylsulphamoyl benzamide and pharmacologically acceptable salts thereof.

2. The method of claim 1 wherein the benzamide is administered to the subject at a dosage from 15 to 150 milligrams per day.

* * * * *